US009860302B2

(12) United States Patent
Wittner et al.

(10) Patent No.: US 9,860,302 B2
(45) Date of Patent: Jan. 2, 2018

(54) METHOD, CONTROL MODULE, APPARATUS AND SYSTEM FOR TRANSFERRING DATA

(75) Inventors: Bernd Wittner, Malmo (SE); Jacob Kroon, Malmo (SE)

(73) Assignee: Gambro Lundia AB, Lund (SE)

( * ) Notice: Subject to any disclaimer, the term of this patent is extended or adjusted under 35 U.S.C. 154(b) by 628 days.

(21) Appl. No.: 14/004,044

(22) PCT Filed: Mar. 8, 2012

(86) PCT No.: PCT/EP2012/053998
§ 371 (c)(1),
(2), (4) Date: Nov. 13, 2013

(87) PCT Pub. No.: WO2012/120078
PCT Pub. Date: Sep. 13, 2012

(65) Prior Publication Data
US 2014/0115101 A1 Apr. 24, 2014

Related U.S. Application Data

(60) Provisional application No. 61/450,182, filed on Mar. 8, 2011.

(30) Foreign Application Priority Data

Mar. 8, 2011 (SE) ...................................... 1150202

(51) Int. Cl.
*G06F 17/00* (2006.01)
*H04L 29/08* (2006.01)
*G06F 19/00* (2011.01)

(52) U.S. Cl.
CPC .......... *H04L 67/10* (2013.01); *G06F 19/3412* (2013.01); *G06F 19/3481* (2013.01);
(Continued)

(58) Field of Classification Search
USPC ......... 235/462.08, 375, 462.01–462.09, 383; 705/2, 3
See application file for complete search history.

(56) References Cited

U.S. PATENT DOCUMENTS 5,609,770 A * 3/1997 Zimmerman ........... A61M 1/16
210/143
5,679,245 A * 10/1997 Manica ................... A61M 1/16
210/134
(Continued)

FOREIGN PATENT DOCUMENTS

CN 101882209 11/2010
CN 102170492 8/2011
(Continued)

OTHER PUBLICATIONS

European International Search Report dated Oct. 31, 2013, cited in PCT/EP2012/053998.

*Primary Examiner* — Tuyen K Vo
(74) *Attorney, Agent, or Firm* — K&L Gates LLP

(57) ABSTRACT

A method, control module and extracorporeal blood treatment apparatus are provided for transferring data from said extracorporeal blood treatment apparatus. Data is retrieved pertaining to an operation of the apparatus, the data is encoded into a machine readable graphical representation for decoding at a remote server to recover the retrieved data and displaying the machine readable graphical representation as an image on the display to allow capture of the displayed image with an image capturing device and transmission of the image from the image capturing device to a remote server over a communication channel.

29 Claims, 7 Drawing Sheets

(52) U.S. Cl.
CPC ...... *F04C 2270/041* (2013.01); *G06F 19/323* (2013.01); *G06F 19/3418* (2013.01)

(56) References Cited

U.S. PATENT DOCUMENTS

| | | | |
|---|---|---|---|
| 5,923,834 A * | 7/1999 | Thieret | G03G 15/55 399/8 |
| 7,848,578 B2 | 12/2010 | Suomela et al. | |
| 8,125,663 B2 * | 2/2012 | Yamada | H04N 1/00344 358/1.14 |
| 2002/0151804 A1 * | 10/2002 | O'Mahony | A61M 1/16 600/504 |
| 2003/0154108 A1 * | 8/2003 | Fletcher-Haynes | G06Q 50/24 705/3 |
| 2004/0186357 A1 * | 9/2004 | Soderberg | A61B 5/00 600/300 |
| 2004/0260803 A1 * | 12/2004 | Nakamura | G06K 15/00 709/224 |
| 2005/0079511 A1 | 4/2005 | Mandema et al. | |
| 2006/0000910 A1 | 1/2006 | Chong et al. | |
| 2006/0196950 A1 * | 9/2006 | Kiliccote | G06K 7/14 235/494 |
| 2007/0017996 A1 | 1/2007 | Xia et al. | |
| 2007/0213938 A1 | 9/2007 | Kai | |
| 2008/0130896 A1 * | 6/2008 | Wernet | H04L 9/3226 380/277 |
| 2008/0250122 A1 | 10/2008 | Zsigmond et al. | |
| 2010/0163613 A1 | 7/2010 | Bucher et al. | |
| 2011/0029748 A1 * | 2/2011 | Nakamura | G06F 11/1451 711/162 |
| 2011/0112405 A1 * | 5/2011 | Barthe | A45D 44/005 600/459 |
| 2011/0207531 A1 * | 8/2011 | Gagner | G07F 17/3248 463/30 |

FOREIGN PATENT DOCUMENTS

| | | |
|---|---|---|
| EP | 0 240 101 A2 | 10/1987 |
| EP | 1 724 986 A1 | 11/2006 |
| JP | 2001-346870 | 12/2001 |
| JP | 2007-28575 | 2/2007 |
| JP | 2007-185851 | 7/2007 |
| JP | 2008-067878 | 3/2008 |
| JP | 2008-124648 | 5/2008 |
| JP | 2003-205031 | 7/2008 |
| WO | 2004092853 A2 | 10/2004 |
| WO | 2005031628 A1 | 4/2005 |
| WO | 2005/104033 | 11/2005 |
| WO | 2006021154 A1 | 3/2006 |
| WO | 2007023329 A1 | 3/2007 |
| WO | 2008125997 A1 | 10/2008 |
| WO | 2010097618 A1 | 9/2010 |

* cited by examiner

METHOD, CONTROL MODULE, APPARATUS AND SYSTEM FOR TRANSFERRING DATA

CROSS RELATED APPLICATION

This application is the U.S. national phase of International Application No. PCT/EP2012/053998 filed 8 Mar. 2012 which designated the U.S. and claims priority to U.S. Patent Application Ser. No. 61/450,182 filed 8 Mar. 2011 and Swedish Patent Application No. 1150202-8 filed 8 Mar. 2011, the entire contents of all of which applications are hereby incorporated by reference.

TECHNICAL FIELD

This invention pertains in general to the field of apparatuses for extracorporeal blood treatment. More particularly the invention relates to transfer of data related to operation of such apparatuses.

Specifically, though not exclusively, the invention is usefully applied in the field of dialysis monitors, such as for example machines for intensive care of acute renal failure.

BACKGROUND

Around the world, there are a vast number of apparatuses for extracorporeal blood treatment in hospital, clinical and home environments. Due to continuous product development within the field, such as improvement of software and/or hardware, the exact configuration of each individual apparatus may vary greatly. Geographical and regulatory differences also make it virtually impossible to have uniform software/hardware profile of apparatuses, even if they are manufactured around the same point in time.

Efficient data handling, such as gathering of statistical and/or maintenance information of such apparatuses requires up-to date information on the device status and configuration, i.e. knowledge of installed components, software versions etc. Reports on operative irregularities and malfunctions are cumbersome for nurses and hospitals to deal with. Retrieval of device information is time-consuming but necessary to be able to diagnose the problem correctly, given the abovementioned variation of existing software/hardware configurations. As a consequence, service technicians are often sent out to resolve minor issues which could have been handled by clinical staff, had only the knowledge of the device information been sufficient. Also, when waiting for technicians to arrive, the apparatuses may be out of service. If so, apparatuses are unavailable for patient treatment and increase costs and strain on hospitals and clinics. Thus, there is a need for remote retrieval of device information from the apparatuses.

Over time, attempts have been made to facilitate device information retrieval. Solutions include various connections to the interface of apparatuses, such as Ethernet, USB, card slots, etc. However, for security reasons hospitals are reluctant to allow access to their networks and retrieval of information via USB and card slots are cumbersome and require certain skills from the clinical staff, skills which are often not readily available. Thus, even though the apparatuses may be connected to a local network, this is typically not open to remote access.

For these purposes, an apparatus for extracorporeal blood treatment is typically not able to establish remote communication channels, since it cannot be connected via wireless networks, due to risk of electronic interference, and at the same time cannot be plugged into land-based networks, accessible from the outside, due to security/privacy restrictions. Thus, an apparatus for extracorporeal blood treatment is usually configured to display information on a display via a graphical user interface. This allows for a local visual communication with a user.

However, such local visual communication may often be perceived as disturbing and/or stressful by a user, since it often interferes with normal operation. Error messages suddenly appearing on the display of an apparatus for extracorporeal blood treatment are likely to confuse the device operator who may only be trained to handle normal operation of the apparatus.

Hence, an improved system for transferring data related to the operation of an extracorporeal blood treatment apparatus would be advantageous.

There is a need for a new method, apparatus and system for transferring data from an extracorporeal blood treatment apparatus and in particular it would be advantageous with a method, apparatus and system for improving retrieving apparatus related data, allowing increased flexibility, safety, security, user friendliness and/or cost-effectiveness.

SUMMARY OF THE INVENTION

The present invention preferably seeks to mitigate, alleviate or eliminate one or more of the above-identified deficiencies in the art and disadvantages singly or in any combination and solves at least the above mentioned problems by providing a method, a control module, an extracorporeal blood treatment apparatus, a system and a computer-readable medium according to the appended patent claims.

The general solution according to the invention is to transfer data from an extracorporeal blood treatment apparatus comprising a display, via displaying of the data on the display in the form of a machine readable graphical representation, to allow capture of the displayed image with an image capturing device and transmission of the image from the image capturing device to a remote server over a communication channel.

According to a first aspect, a method is provided for transferring data from an extracorporeal blood treatment apparatus comprising a display and at least one control unit. The method comprises retrieving data from the control unit, encoding the data into a machine readable graphical representation adapted for decoding at a remote server to recover the retrieved data, and displaying the machine readable graphical representation as an image on the display to allow capture of the displayed image with an image capturing device and transmission of the image from the image capturing device to said remote server over a communication channel.

According to a second aspect, there is provided a method for receiving data at an extracorporeal blood treatment apparatus comprising a camera or scanner and at least one control unit. The method comprises acquiring an image of a machine readable graphical representation; decoding data of the machine readable graphical representation; and adapting controlling of the operation of the apparatus based on the decoded data.

According to a third aspect, there is provided a method for exchanging data for an extracorporeal blood treatment apparatus comprising a display, a camera or scanner and at least one control unit. The method comprises transferring data according to the method of the first aspect; and receiving data according to the method of the second aspect.

According to a fourth aspect, a control module for use in an extracorporeal blood treatment apparatus is provided. Said control module comprises a control unit and an operating system, and is configured to retrieve data pertaining to an operation of the apparatus and encode the data into a machine readable graphical representation adapted for presentation on a display, and further adapted for decoding at a remote server to recover the retrieved data. The control module may be configured to acquire an image of a machine readable graphical representation; decode data of the machine readable graphical representation; and adapt controlling of the operation of the apparatus based on the decoded data.

According to a fifth aspect, an extracorporeal blood treatment apparatus is provided, comprising the control module according to the fourth aspect of the invention and a display.

According to a sixth aspect, a system for transferring data related to the operation of an extracorporeal blood treatment apparatus is provided. The system comprises an extracorporeal blood treatment apparatus adapted to perform the method according to the first aspect of the invention, an image capturing device and a remote server connected to a communication network. The image capturing device is adapted to capture the image displayed on the display of the extracorporeal blood treatment apparatus and transmit the captured image to said remote server over a communication channel on the communication network, and the remote server is adapted to receive the transmitted image and decode it to recover the retrieved data.

According to a seventh aspect, a computer-readable medium for processing by a computer is provided. Said computer-readable medium has embodied thereon a computer program for transferring data from an extracorporeal blood treatment apparatus comprising a display and at least one control unit. The computer program comprises a first code segment for retrieving data pertaining to an operation of the apparatus, a second code segment for encoding the data into a machine readable graphical representation adapted for decoding at a remote server to recover the retrieved data, and a third code segment for displaying the machine readable graphical representation as an image on the display to allow capture of the displayed image with an image capturing device and transmission of the image from the image capturing device to said remote server over a communication channel.

According to an eighth aspect, there is provided a computer program comprising program code which when executed by processor of a control module of an extracorporeal blood treatment apparatus causes the control module to perform the method according to any of the first, second or third aspects.

Further embodiments of the invention are defined in the dependent claims.

One of the problems/deficiencies which may be solved by embodiments of the present invention is that it allows easier, faster and more robust handling of information, which increases flexibility and cost-effectiveness. Since the data is displayed as a machine readable graphical representation, a user does not need to interpret the data, which avoids confusion and human error, thus increasing safety and security. The possibility to use commodity hardware as image capturing devices, such as digital cameras commonly found in today's mobile phones, instead of specialised reading devices, facilitates serviceability and enhances user compliance. Display of data also enables remote information access. It may also enable data logging. Also, since the data is only displayed on the display and not sent by means of e.g. a wireless transmitter, the apparatus does not transmit any signals, which may otherwise disturb surrounding electronic equipment. This leads to safer operation of the apparatus.

Embodiments of the fourth to eighth aspects may correspond to the above-identified embodiments of the first, second and third aspects.

BRIEF DESCRIPTION OF THE DRAWINGS

These and other aspects, features and advantages of which the invention is capable will be apparent and elucidated from the following description of embodiments of the present invention, reference being made to the accompanying drawings, in which.

DESCRIPTION OF EMBODIMENTS

Several embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention.

The following description focuses on an embodiment of the present invention applicable to an apparatus for extracorporeal blood treatment and in particular to a dialysis monitor. However, it will be appreciated that the invention is not limited to this application but may be applied to many other medical devices including for example liver treatment devices or ultrafiltration devices.

Figure 1:
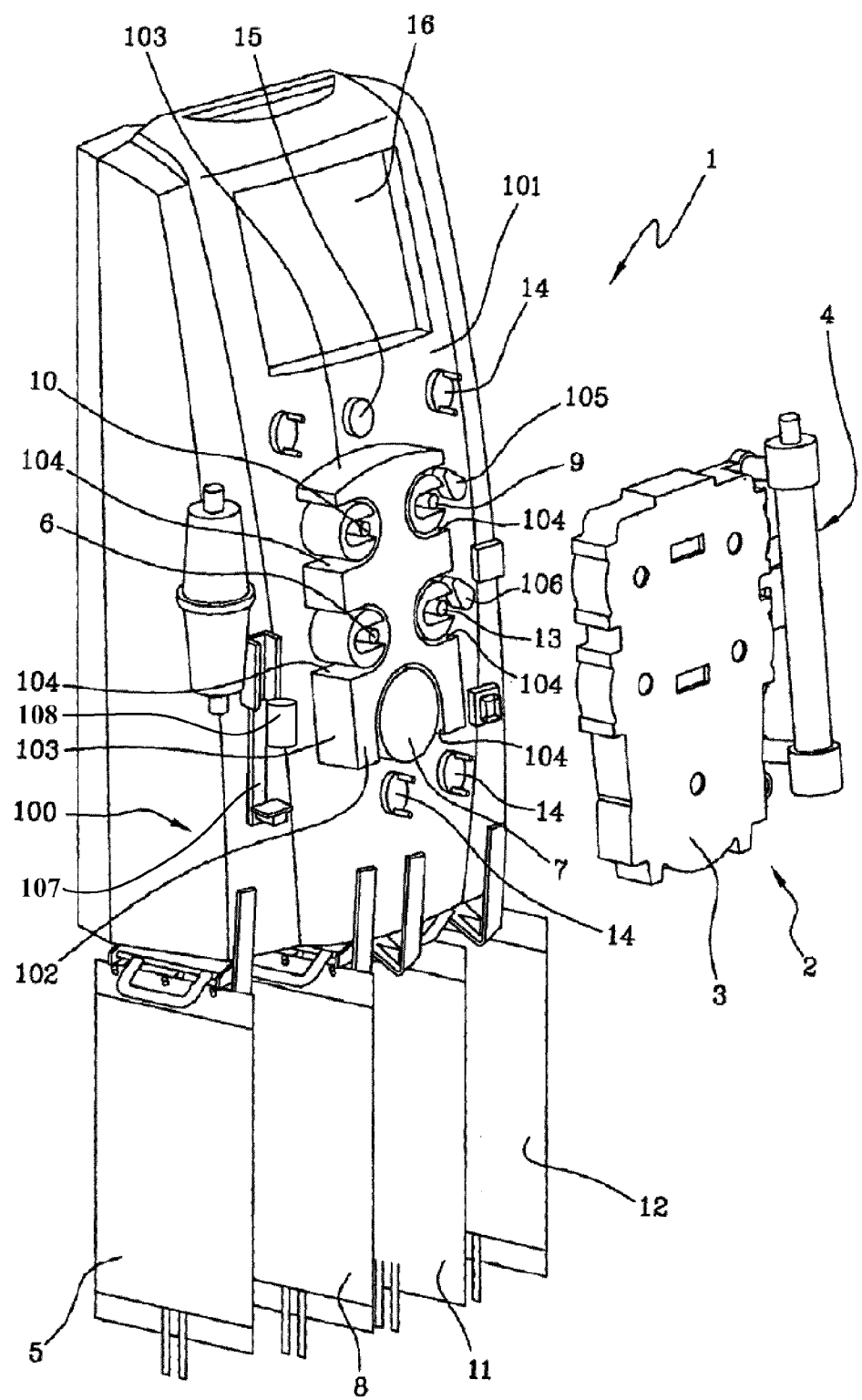
FIG. 1 is an illustration of a dialysis monitor according to an embodiment.

In an embodiment of the invention according to FIG. 1, reference numeral 1 denotes in its entirety an apparatus for extracorporeal blood treatment, represented in the illustrated embodiment by a dialysis monitor which is suitable for intensive treatment of acute kidney failure. Reference numeral 2 denotes in its entirety an integrated module which can be coupled to the dialysis monitor 1.

The integrated module 2 is constituted by a combination of at least one support element 3, a distribution circuit (of known type and not illustrated) arranged on the support element 3, and a blood treatment unit 4. The blood treatment unit 4 can be, for example, a plasma filter, a hemodialysis filter, a hemofiltration filter, or a different unit.

The hydraulic circuit, which is completed by a combination of the integrated module 2 and the monitor 1, comprises a blood circuit which removes blood from a patient, for example via a catheter inserted in a vascular access of the patient, and takes the blood though a blood removal line to the treatment unit 4.

The blood passes through a first chamber (blood chamber) of the treatment unit 4 and, via a return line, is transported back to the patient.

Immediately downstream of the blood removal zone, connection is made between the removal line and an auxiliary pre-infusion line.

In particular, the monitor 1 includes at least one container of a first sterile fluid 5 for supplying the pre-infusion line; fluid transport means, in the embodiment constituted by a pre-infusion pump 6, for example a peristaltic pump, controlling the flow of fluid in the pre-infusion line directly into the blood via a direct connection to the blood removal line, at least one blood pump 7 for control and management of a correct blood flow in the circuit. The blood pump 7 may be peristaltic.

Generally the container of the first sterile fluid 5 can contain a pre-infusion fluid, although the same container can be used for containing an anticoagulant, usually of a locally-acting type.

Once a blood circulation direction has been established from the blood removal zone to the blood treatment unit 4, and thereafter to the blood return line towards the patient, a blood pressure sensor is included immediately downstream of the auxiliary pre-infusion line.

Continuing along the blood circulation direction, a device 107 is included for administration of a substance such as an anticoagulant or calcium, for example a syringe containing appropriate doses of heparin, operably connected to a pump for filling/emptying the syringe. The device 107 may also be a scale or a pressure gauge. In an embodiment, the device 107 infuses heparin, i.e. is a heparin infusion device.

In an embodiment, several devices 107 may be included for independent administration of several substances.

The blood then crosses a further pressure sensor which monitors the correct flow rate internally of the blood circuit.

After crossing the first blood chamber of the treatment unit 4, where substance-exchange and molecular and fluid exchange takes place through a semi-permeable membrane, the treated blood enters the return line, crossing a gas separator (generally air), where any air bubbles present or introduced to the blood during treatment are expelled.

The treated blood exiting from the gas separator (also known as a deaeration chamber) crosses a bubble sensor (also known as an air detector) which checks that these dangerous formations are not present in the treated blood, which is about to be sent back into the blood circuit of the patient.

Immediately downstream of the bubble sensor a closure element is located, which on activation of an alarm can block the blood flow towards the patient. In particular, if the bubble sensor reveals the presence of anomalies in blood flow, the monitor 1, the blood passage would immediately be stopped by means of the closure element (which can be a cock, a clamp or the like), in order to prevent any kind of consequence to the patient. Downstream of the closure element the treated blood is returned to the patient undergoing treatment.

The distribution circuitry comprises a first circuit of a second sterile fluid (dialyzing liquid) having at least one inlet line to the blood treatment unit 4 and an outlet line from the treatment unit 4.

At least one container of the second sterile fluid 8 is destined to supply the inlet line of the first circuit.

The inlet line is destined to cooperate with means for fluid transport, being at least one pump 9 (in the embodiment a peristaltic pump) predisposed on the frontal part of the monitor 1 to control the flow of the second sterile fluid coming from the container 8, and to define a circulation direction. Downstream of the pump 9 of the second sterile fluid, along the circulation direction, a branch is included which divides the first circuit of the second sterile fluid into an inlet branch and an infusion branch.

In particular the infusion branch is connected to the blood circuit return line. In other words, with this infusion line infusion can be made directly into the blood, using the contents of the container 8 of the second sterile fluid.

The inlet branch takes the second sterile fluid directly to the blood treatment unit 4, in particular to a second chamber (dialysis chamber) of the unit 4.

The first circuit of the second sterile fluid is further associated to a first selector which determines the percentage quantities of fluid flow into the infusion branch and the inlet branch.

Generally, the first selector, usually located in proximity of the branch, enables selection between at least a first operative condition, in which the second sterile fluid can pass into the inlet branch but cannot pass into the infusion branch, and a second operative condition, in allowing passage of fluid into the infusion branch but not into the inlet branch. In other words the first selector can be constituted by a valve element suitable for operating in a fluid circuit, which can alternatively shut off passage of fluid into one or the other branch.

The second sterile fluid (dialyzing liquid) crosses the inlet branch and enters the second chamber (dialysis side) of the blood treatment unit 4.

In particular the first chamber (blood chamber), crossed by the blood flow, is separated from the second chamber (dialysis chamber), crossed by the second sterile fluid, by a semi-permeable membrane which enables passage of the damaging molecules and substances and fluids in the blood towards the second sterile fluid (dialyzing liquid), mainly through convection and diffusion processes; at the same time, and by the same principles, passage of substances and molecules from the second sterile fluid and towards the blood is allowed.

The second sterile fluid, for dialysis, enters the outlet line of the first circuit and crosses a special pressure sensor for controlling the functioning of the line. Means for transporting the fluid, for example an effluent drainage pump 10, are present, which control the flow in the fluid circuit outlet line. This pump 10, as the others, is usually peristaltic.

The discharge fluid then crosses a blood leak detector 15 and is sent on to an effluent collection container 11.

An infusion line is located on the return line of the blood circuit. In particular, a third sterile fluid (infusion fluid) is sourced from at least one auxiliary container 12 and, by action of a fluid transport means, generally an infusion pump 13 which controls flow (in the embodiment a peristaltic pump), is sent directly to the blood circuit return line.

The third sterile fluid (infusion liquid) can be sent directly into the gas separator device.

The post-infusion branch of the first circuit of the second sterile fluid and the infusion line of the third sterile fluid are provided with a common terminal inlet tract to the blood circuit. The terminal inlet tract is located downstream of the infusion pump 13 with respect to an infusion direction, and sends the fluid directly into the gas separator. At least one pre-infusion branch is present in the infusion line, connected to the blood circuit removal line.

In more detail, there is a branch located downstream of the infusion pump 13 with respect to the infusion direction, which divides the infusion line into a pre-infusion branch and a post-infusion branch.

The pre-infusion branch takes the fluid removed from the container to the blood circuit removal line downstream of the blood pump 7 (downstream with respect to the circulation direction). The post-infusion branch is directly connected to the common terminal tract.

The infusion line further comprises a second selector for determining the percentage quantities of liquid flow to send into the post-infusion branch and the pre-infusion branch. The second selector, located in proximity of the branch, is positionable between at least one first operative configuration, in which fluid can pass into the pre-infusion branch but not the post-infusion branch, and at least a second operative configuration, in which fluid is allowed to pass into the post-infusion branch and not the pre-infusion branch.

As with the first selector on the first circuit of the second sterile fluid, the second selector is able to establish percentages of fluid passing into each of the two branches, and can if necessary vary the times according to the treatments to be carried out. The first and second selectors are usually, but not necessarily, of similar type.

The monitor 1 is provided with means for determining at least the weight of the container of the first sterile fluid 5 and/or the container of the second sterile fluid 8 and/or the container of the third sterile fluid 12 and/or the discharge container 11. The means for determining are constituted by weight sensors, for example scales (at least one independent scales for each container or fluid bag associated to the monitor 1).

There will be at least four of these scales present, each independent of the others, and each predisposed to measure the respective weight of a container 5, 8, 11, 12.

In FIG. 1, reference 16 denotes a display, which is part of a user interface (not shown) of the monitor 1. In FIG. 1, the display 16 is a touch display and is connected to the control module (not shown), which is programmed to display on the display 16 a plurality of display screens, areas or windows in sequence or simultaneously, so that the display 16 is divided into several distinct areas displaying distinct information.

In the present description, the term "touch display" refers to a device having a display for data output, which is also used for input through selection of parts (touch keys or soft keys) of the display screen using the fingers; the device is able to detect where a user has touched the display and from this derive the selected commands and perform them.

The control module is operatively associated with parts of the blood circuit and in particular with the pressure sensor, the blood pump 7, the device 107 for administration of a substance, the further pressure sensor, as well as on the bubble sensor and the closure element. During operation, the control module is thus configured to handle data and control different parts of the monitor 1, such as receive input from said parts and send output to said parts.

The control module is operatively associated with the user interface and is configured to, during operation, receive input from the user interface and send output to the user interface, such as to the display 16.

Figure 2:
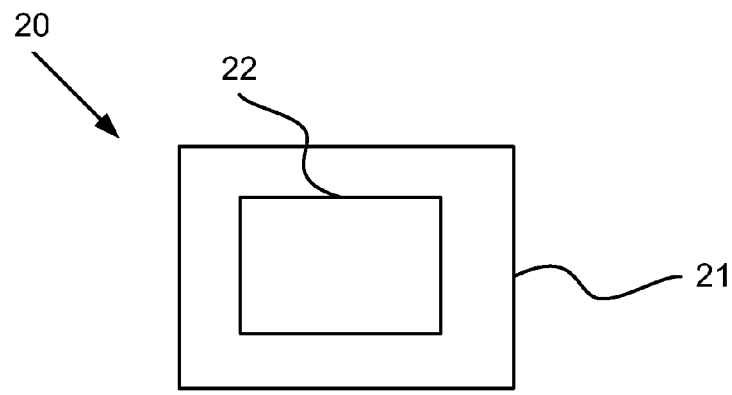
FIG. 2 is a schematic overview of a control module according to an aspect.

FIG. 2 shows a schematic overview of a control module 20 according to an embodiment. The control module 20 comprises a control unit 21 and an operating system 22.

Figure 3:
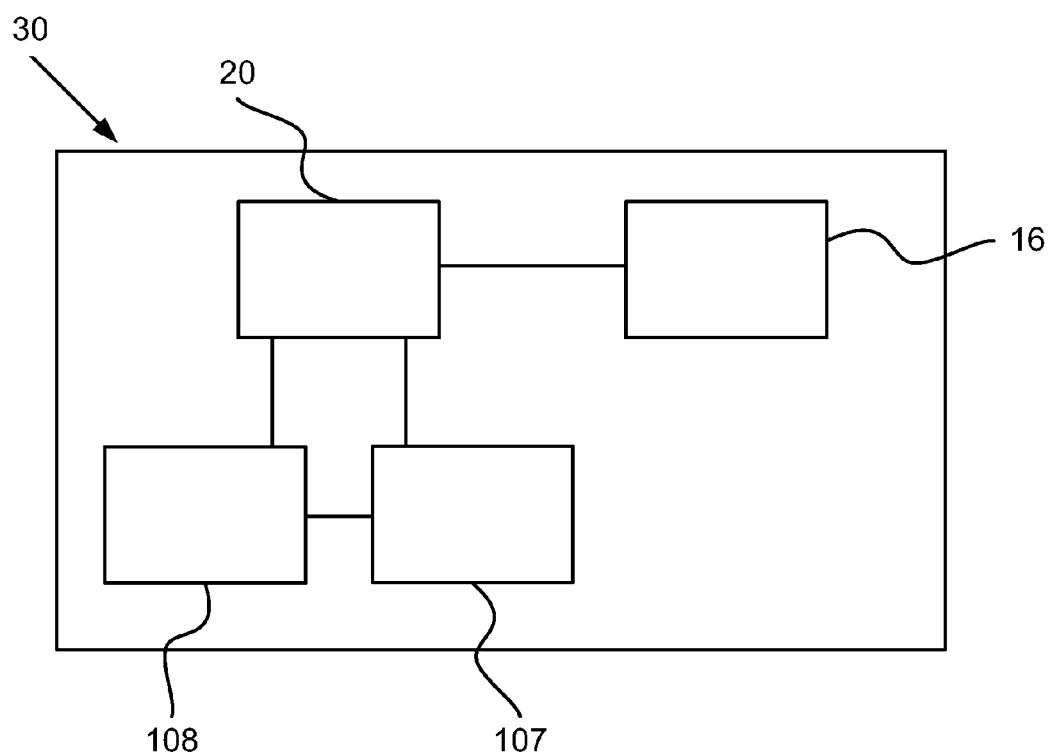
FIG. 3 is a schematic overview of an extracorporeal blood treatment apparatus according to an aspect.

FIG. 3 discloses a schematic overview of an extracorporeal blood treatment apparatus 30, such as the monitor 1, comprising a control module 20 and a display 16.

The apparatus 30 is configured so that the control module 20 may receive input from a user interface, which comprises said display 16, as well as send instructions to the user interface. The user interface may have an actuator element for triggering the performance of the control module 20. The control module 20 may also control the operation of the parts of the apparatus 30, such as the device 107 for administration of a substance. The control module 20 may also receive input from the components of the apparatus 30, such as the sensor 108, which is monitoring the device 107 for administration of a substance, as well as send instructions to the sensor 108 and the display 16.

Figure 4:
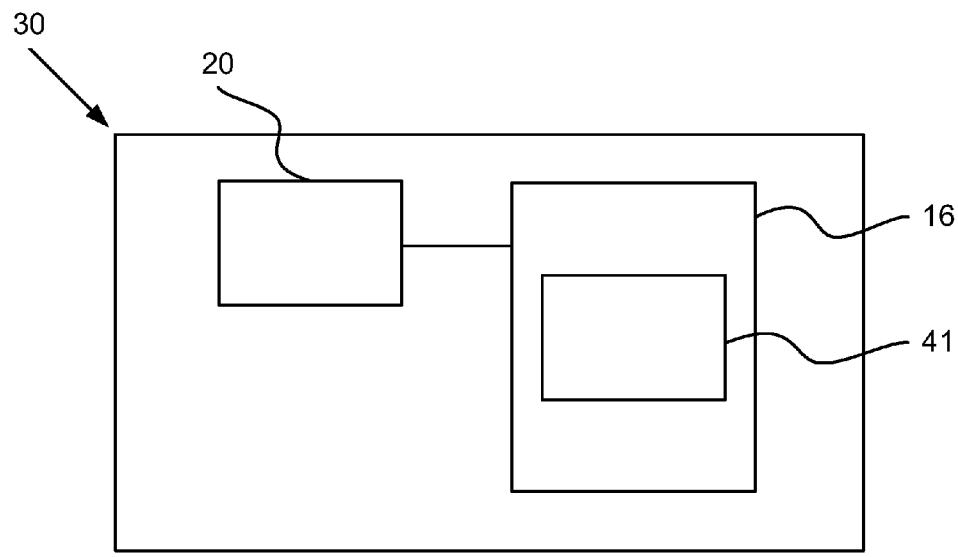
FIGS. 4-5 are schematic overviews of an extracorporeal blood treatment apparatus according to different embodiments.

As shown in FIG. 4, the control module 20 may be arranged in the extracorporeal blood treatment apparatus 30, and configured to retrieve data pertaining to an operation of the apparatus, such as from one or several control unit/s of the monitor 1 and encode the data into a machine readable graphical representation 41 adapted for display on the display 16, and further adapted for decoding at a remote server (not shown) to recover the retrieved data.

Data pertaining to an operation of the apparatus may be any kind of data relevant for the use and operation of the apparatus. As non-limiting examples, the data may be usage specific, such as usage history, operator interaction history, and treatment parameters, or machine specific for said apparatus such as machine ID, such as a serial number, machine configuration data and machine status data, or any combination of such data types. Machine configuration data may involve hardware and software versions.

The data pertaining to an operation may also be data regarding status and/or function of different components of the apparatus, described in relation to FIG. 1 above, how they interact and how they operate.

The data pertaining to an operation may be retrieved from single parts of the apparatus such as serial number, unlocked software features etc., or from a combination of parts, i.e. subsystems such as peripheral features or external equipment. Examples of peripheral systems are slang sets, air bubble detector, scales, syringe pumps or sensors. Thus, it is possible to create a configuration fingerprint, which is based on the specific hardware components and/or software features for a particular apparatus. The subsystems may comprise one or more control modules, which may transmit and/or process the data.

In an embodiment, the control module 20 is configured to retrieve data in form of a serial number of the apparatus 30, output the data to a PCMCIA log file and encode the data as a QR barcode, which is saved as an image in BMP format. The control module 20 is further configured to display the BMP image on the display 16, as part of the graphical user interface of the apparatus 30.

Figure 5:
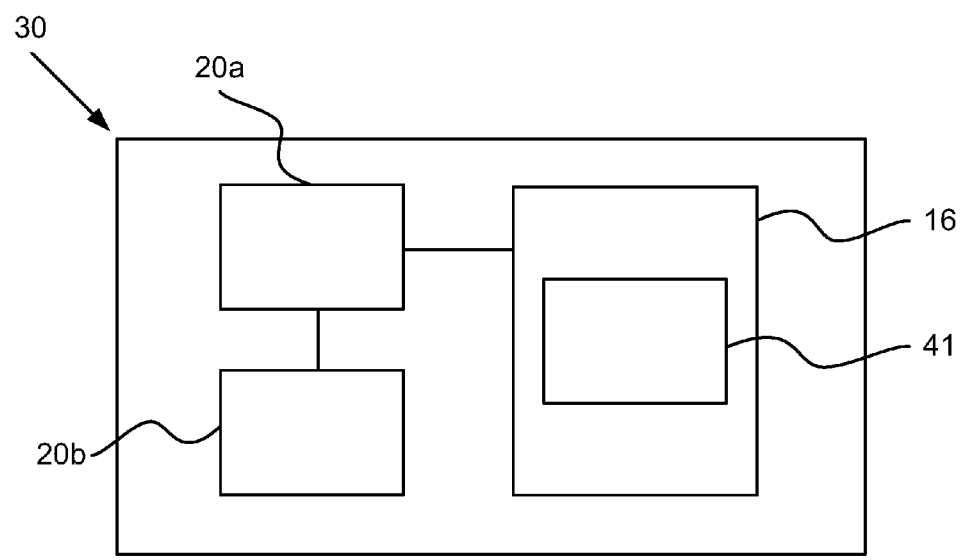

In an embodiment according to FIG. 5, the extracorporeal blood treatment apparatus 30 comprises a first control module 20*a* and a second control module 20*b*, i.e. at least two modules. The second control module 20*b* may be connected to different parts of the apparatus (not shown), as well as to the first control module 20*a*. The first control module 20*a* is configured to retrieve data pertaining to an operation of at least one blood treatment apparatus/es, such as the monitor 1, optionally via the second control module 20*b*, and encode the data into a machine readable graphical representation 41 adapted for display on the display 16, and further adapted for decoding at a remote server (not shown) to recover the retrieved data.

As will be appreciated by the person skilled in the art, a number of possible combinations and configurations of control modules 20 in the extracorporeal blood treatment apparatus 30 may vary, as required by the circumstances and the desired functions and components of the extracorporeal blood treatment apparatus 30.

The machine readable graphic representation may be e.g. a barcode image or a two-dimensional matrix code image.

The two-dimensional matrix code image may be any kind of two-dimensional matrix code image, such as selected from the group consisting of: 3-DI, ArrayTag, Aztec Code, Chromatic Alphabet, Codablock, Code 1, Code 16K, Code 49, ColorCode, Compact Matrix Code, CP Code, CyberCode, DataGlyphs, Datamatrix, Data Matrix ECC200, Datastrip Code, Dot Code A, d-touch, EZcode, Grid Matrix Code, High Capacity Color Barcode, HueCode, INTACTA. CODE, InterCode, JAGTAG, MaxiCode, mCode, MicroPDF, MiniCode, MMCC, Optar, PaperDisk, PDF417, PDMark, QR Code, QuickMark Code, ShotCode, Small Aztec Code, SmartCode, Snowflake Code, SPARQCode, SuperCode, Trillcode, UltraCode, UnisCode, WaterCode, VeriCode, VSCode.

In an embodiment, the control module 20 is further configured to analyse the data before encoding and control the displaying of the machine readable graphical representation depending on an outcome of the data analysis. This enables display differentiation depending on data type, e.g. so that some data that is considered critical based on some predefined criterion renders a predominant display, while other data may render a much more modest display, or even no display at all.

The information to be retrieved may also be controlled by user input, i.e. that the user selects certain kinds of information desired, which the controller 20 retrieves and encodes for display. Thus, the information may be pre-processed, and specific information selected for further data handling by the controller. In an embodiment, such specific desired information sets may be saved. This is advantageous, because the sets can then be reused and the user only needs to request the information set and not repeatedly specify the desired information.

The control module 20 may also be configured to encode the data into at least two machine readable graphical representations, adapted for sequential display on the display 16 as a film and further adapted for decoding at a remote server to recover the retrieved data. An advantage with this is that more data may be displayed and thus transferred to a remote server.

The control module 20 of the extracorporeal blood treatment apparatus 30 may be configured to store said at least two machine readable graphical representations in a database. An advantage with this is that it allows retrieval of data history, such as operation history of the apparatus, treatment statistics, overview of hardware/software components in use and/or material used with the apparatus (tubes, liquids etc.)

In an embodiment (not shown) the control module 20 is configured to store the retrieved data in a database for subsequent encoding and displaying at a later time. This may save data storage capacity, since the retrieved data may require less memory than the machine readable graphical representation. The fact that data has been retrieved, awaiting encoding and displaying, may be indicated by i.e. a time stamp displayed somewhere on the display 16.

The control module 20 may be configured to display, on the display 16, the machine readable graphical representation without interfering with the operation of the extracorporeal blood treatment apparatus. This is advantageous, since the user will then be able to access the data from the machine readable graphical representation without having to abort the normal operation of the apparatus, which may run a treatment cycle lasting up to several days.

Reverting back to FIG. 1, the control module (not shown) is also used for controlling the first circuit of the second sterile fluid, and in particular to receive data sent by the scales relating to the weight of the container 8; it is also operatively associated to the pump 9, the first selector, the pressure sensor, the drainage pump 10 and the scales weighing the effluent discharge container 11.

The control module is also operatively associated to the infusion line of the third sterile fluid, monitoring the weight of the container 12 (measured by a scale), and also controls the infusion pump 13 and the second selector.

Finally, the control module is operatively associated to the auxiliary line for pre-infusion of the first sterile fluid, measuring the weight of the container 5 via scales and commanding the pre-infusion pump 6 according to the treatment to be carried out.

The above, purely descriptive, account of the hydraulic circuitry of the monitor 1 for extracorporeal blood treatment will now be followed by a brief explanation of how the control module, apparatus and system functions.

The control unit 21 of the control module 20 may be a unit normally used for performing the involved tasks, e.g. a hardware, such as a processor with a memory. The processor may be any of variety of processors, such as Intel or AMD processors, microprocessors, Programmable Intelligent Computer (PIC) microcontrollers, Digital Signal Processors (DSP), etc. However, the scope of the invention is not limited to these specific processors. The memory may be any memory capable of storing information, such as Random Access Memories (RAM) such as, Double Density RAM (DDR, DDR2), Single Density RAM (SDRAM), Static RAM (SRAM), Dynamic RAM (DRAM), Video RAM (VRAM), etc. The memory may also be a FLASH memory such as a USB, Compact Flash, SmartMedia, MMC memory, MemoryStick, SD Card, MiniSD, MicroSD, xD Card, TransFlash, and MicroDrive memory etc. However, the scope of the invention is not limited to these specific memories.

The operating system 22 may be any kind of software suitable for execution by said control unit 21. The operating system will provide low-level tasks such as memory handling, I/O communication, etc. Furthermore, the operating system will support execution of higher-level programs which in turn may control the various parts, components and elements of the apparatus 30/monitor 1.

Normal Operation

Before the actual treatment begins, the apparatus must be prepared. The whole hydraulic circuitry and the treatment unit are correctly associated to the monitor 1 so that the various peristaltic pumps engage the respective tracts of tubing, and all the sensors are correctly positioned; also, the relative bags containing the various fluids are joined up to the respective supply or receiving lines of the liquids, and the blood circuit is connected up to an artery or vein of the patient. When set-up is complete, an initial circulation of the blood internally of the respective circuit is made.

According to the type of treatment selected (pure ultrafiltration, hemodialysis, hemofiltration, hemodiafiltration, etc.), the apparatus for extracorporeal blood treatment 30, such as the monitor 1, is automatically activated and controlled by the control module 20.

The monitor 1 exhibits a machine body 100 provided, on a front surface 101 thereof, with peristaltic pumps 6, 7, 9, 10, 13, destined to cooperate in use with respective tracts of U-shaped tubing on the integrated module.

The machine body 100 exhibits a relief acting as a positioning guide 102 which projects from the front surface 101, which is complementarily shaped with respect to the support element 3 with which it will couple in use.

In other words, the guide 102 exhibits a lateral surface 103 which, when the integrated module is coupled thereto, is contained within a perimeter wall of the support element 3.

The peristaltic pumps also project from the front surface 101 of the machine body 100 and at least a part of the lateral surface of the pumps is complementarily shaped with respect to the perimeter wall of the support element 3.

The projecting peristaltic pumps and the guide 102 in combination define seatings 104 having a semicircular shape, i.e. a U-shape, which seatings 104 are destined to receive the corresponding tracts of U-shaped tubing of the circuitry.

A first mobile element 105 and a second mobile element 106, substantially identical and borne directly on the machine body 100, are destined to be operatively associated to the infusion and/or inlet branch of the second sterile fluid (the first mobile element 105) and, respectively, on the pre-infusion branch and/or the post-infusion branch of the third sterile fluid (the second mobile element 106). In particular the first and second selectors can be constituted by the mobile elements 105, 106, destined to be controlled by the control module 20 to selectively allow or block passage of fluid into one or another of the branches.

The front surface of the apparatus further exhibits a plurality of fastening elements 14 for fixing the pressure sensors; the pressure sensors associated to the circuitry of the integrated module are here connected to the control module 20.

The blood leak detector 15 is also predisposed on the front surface of the apparatus, and during the apparatus preparation process is associated to the fluid circuit in outlet from the treatment unit 4.

A sensor 108 is located in proximity to the device 107 for administration of a substance, so that the sensor may measure parameters related to the device 107 for administration of a substance.

In an embodiment, multiple sensors 108 are located either integrated in the device 107 for administration of a substance and/or in the proximity to the device 107 for administration of a substance, so that the sensors may measure single or multiple parameters related to the device 107 for administration of a substance.

The monitor 1 is configured so that the control module 20 may receive input from the user interface, as well as send instructions to the user interface. The control module 20 also controls the operation of the parts of the monitor 1, such as the device 107 for administration of a substance. The control module 20 may also receive input from the components of the monitor, such as the sensor 108, which is monitoring the device 107 for administration of a substance. The control module 20 may also send instructions to the sensor 108 and the display 16.

During priming and/or operation, the control module 20 is configured to handle information via data transfer.

Data Transfer

The data transfer is executed by the apparatus 30 for extracorporeal blood treatment, such as the monitor 1, controlled by the control module 20, but may be triggered both by the apparatus 30, such as via a control module 20, and by a user.

Figure 6:
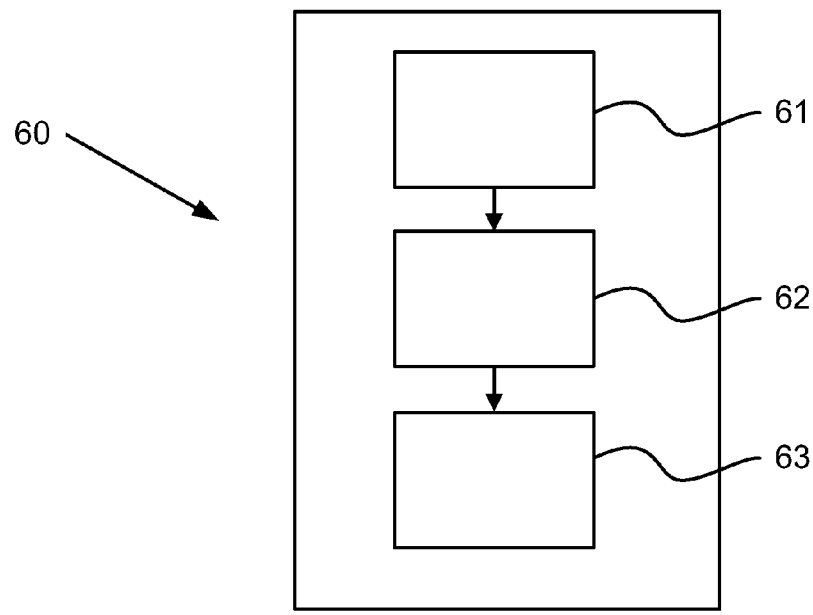
FIG. 6 is a flowchart showing a method according to an aspect.

FIG. 6 gives a schematic overview of a method 60 for transferring data from an extracorporeal blood treatment apparatus 30 comprising a display 16 and at least one control unit 20. The method comprises a step of retrieving 61 data pertaining to an operation of the apparatus, a step of encoding 62 the data into a machine readable graphical representation 81, 91 adapted for decoding at a remote server 1003 to recover the retrieved data, and a step of displaying 63 the machine readable graphical representation as an image on the display to allow capture of the displayed image with an image capturing device and transmission of the image from the image capturing device to said remote server 1003 over a communication channel.

An advantage with this is easier handling of information. Since the data is displayed as a machine readable graphical representation, a user does not need to bother interpreting the code, which avoids confusion. Display of data also enables remote information access. It may also enable data logging. Also, since the data is only displayed on the display and not sent by means of e.g. a wireless transmitter, the apparatus does not transmit any signals, which may disturb surrounding electronic equipment. This leads to safer operation of the apparatus.

The method 60 may also comprise a step (not shown) of pre-processing the data before the step of retrieving 61 data pertaining to an operation. In this pre-processing step, exact content of data may be regulated, so that a user may request specifically data relating e.g. to software information. Then, when the method 60 is executed, only software information is retrieved etc.

An advantage with this is that the method may be adapted for different purposes.

The displaying of the machine readable graphical representation may be automatically prompted by the apparatus, such as based on the occurrence of a certain event. In an embodiment, a certain event is preset when configuring the apparatus.

The encoding 62 and/or displaying 63 of the machine readable graphical representation may be decoupled from the step of retrieving 61 data. An advantage with this is that encoding 62 and/or displaying 63, which may require data processing and/or in other ways risk to disturb normal operation of the apparatus, may occur at a later stage, e.g. when the apparatus is idle and plenty of data processing capability is available. This decreases the risk of error and increases safety of operation of the apparatus.

The information to be retrieved may also be controlled by user input, i.e. that the user selects certain kinds of information desired, which the controller 20 retrieves and encodes for display. In an embodiment, such specific desired information sets may be saved. This is advantageous, because the sets can then be reused and the user only needs to request the information set and not repeatedly specify the desired information.

Along with displaying the machine readable graphical representation, the apparatus may be configured to alert a user, e.g. by making a sound. The apparatus may also or alternatively be configured to aid a user when taking a picture of the graphical representation. The aid can comprise instructions about suitable distance, angle and focussing for taking the picture. For the case a sequence of graphical representations, and thus a sequence of pictures, e.g. by video recording or sequential pictures, instructions can be provided to the operator.

Figure 8:
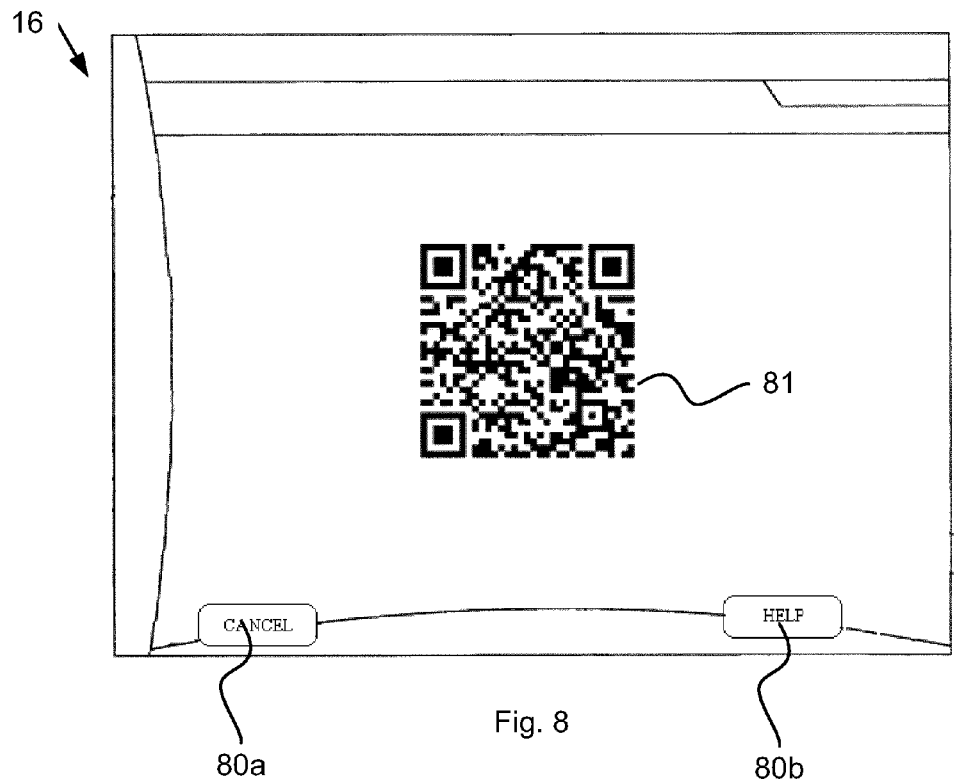
FIGS. 8-9 are schematic examples of display screens.

FIG. 8 is an embodiment showing in principle how the display screen of the display 16 could look after executing the abovementioned method, with the machine readable graphical representation 81 is displayed on the display 16. The display 16 may display various graphic elements, as well as functional elements such as actuator buttons 80a, 80b. These actuator buttons (also called touch keys or soft keys) are data output on the display 16, which are also used for input through selection of parts of the display screen using the fingers; the device is able to detect where a user has touched the display 16 and from this derive the selected commands and perform them. Touching actuator button 80a may e.g. take the user back to the display view displayed during normal operation, simultaneously storing the machine readable graphical representation 81 for later display, and touching actuator button 80b may display a help message, explaining the current view.

The machine readable graphical representation 81 is displayed on the display 16 to allow capture of the displayed image with an image capturing device and transmission of the image from the image capturing device to said remote server 1003 over a communication channel. The machine readable graphical representation 81 is a QR code, which is interpreted as an alphanumerical text string, e.g. "600*****000BAB26588D610401100000Q37JBU7JD QD294B8AFB8AFD294 A226", comprising coded data.

In the abovementioned example, the first three characters represent software version, for example "600" (6.00). The following five characters represent serial number, where "*****" represents the default value "0", followed by twelve characters which represent MAC address, for example "000BAB26588D" (00:OB:AB:26:58:8 D). Next, four characters represent a system date of fingerprint, followed by four characters representing the date of last preventive maintenance. The dates are encoded using four hexadecimal digits, where the first is the number of years passed since 2005 (market introduction), the second represents the month (0-11), and the third and fourth represent the day of the month (1-31). Next, four characters represent e.g. unlocked treatment options and enabled features, encoded in a 16-bit array. After that, eight characters represent calibration data for patient sensor, followed by two characters representing calibration data for air-bubble detector and five times four characters for different firmware settings.

Numerical values are encoded as natural logarithms according to the formula $\ln(x+1)*100$ and the integer part is encoded using a 2 digit base-36 representation. Invalid data (negative or outside the available range) may be encoded as "* *".

An advantage with this is that possible to store much information in a relatively small number of characters.

The alphanumerical text string comprises information that may also, in addition to the machine readable graphical representation 81, be displayed in plain text on the display 16 (not shown).

In an embodiment (not shown) an event, which may be a preset criteria, triggers a specific mode where the monitor displays a prompt for input of information, e.g. parameters for pre-processing of the data. This, so called verbose mode, may then define the content of data to be retrieved. After execution of the method 60, the data is stored and may be displayed when desired.

In an embodiment (not shown) the method 60 is only possible to execute when the apparatus is in a dedicated service mode, which is not possible to access during normal operation, i.e. treatment. Once the method 60 has been executed, the encoded machine readable graphical representation may be displayed even during normal operation, e.g. by a specific page displaying general technical data, but not encoded.

Thus, between the step of retrieving 61 and the step of encoding 62 data pertaining to an operation, the method 60 may further comprise a step of storing the retried data pertaining to an operation in a memory and loading the stored data pertaining to an operation from the memory. The step of storing and the step of loading the data may be temporally separated, i.e. storing data at on time point and loading data at a later time point. An advantage with this is that it allows a temporal decoupling of encoding and displaying since it reduces the risk of disturbing the system during normal operation due to encoding, which may require processor capacity. Instead, the encoding may take place at a later time point, when the apparatus is idle.

Figure 7:
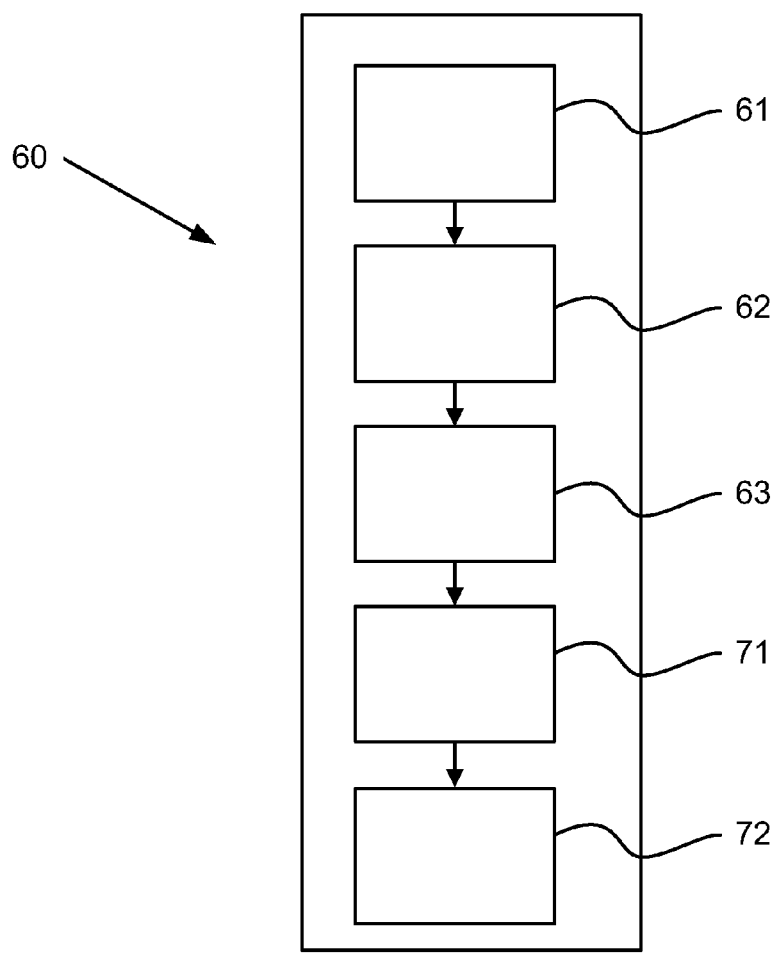
FIG. 7 is a flowchart showing a method according to an embodiment.

In an embodiment according to FIG. 7, the method 60 may further comprise a step of analysing 71 the data before encoding and a step of controlling 72 the displaying of the machine readable graphical representation depending on an outcome of the data analysis.

An advantage with this is that it enables prioritizing of the data display. For example, if the step of analysing 71 the data reveals that the data is critical for the continued operation, such as a severe error, it may be displayed alongside with the regular operational parameters and is thus more easily noted by the user. In an alternative embodiment, the apparatus 30 is operational even though an error message is displayed. Since the machine readable graphical representation is not to be interpreted by the users, they are less likely to be confused compared to the occurrence of a sudden error message displayed alongside with regular operational parameters.

Figure 9:
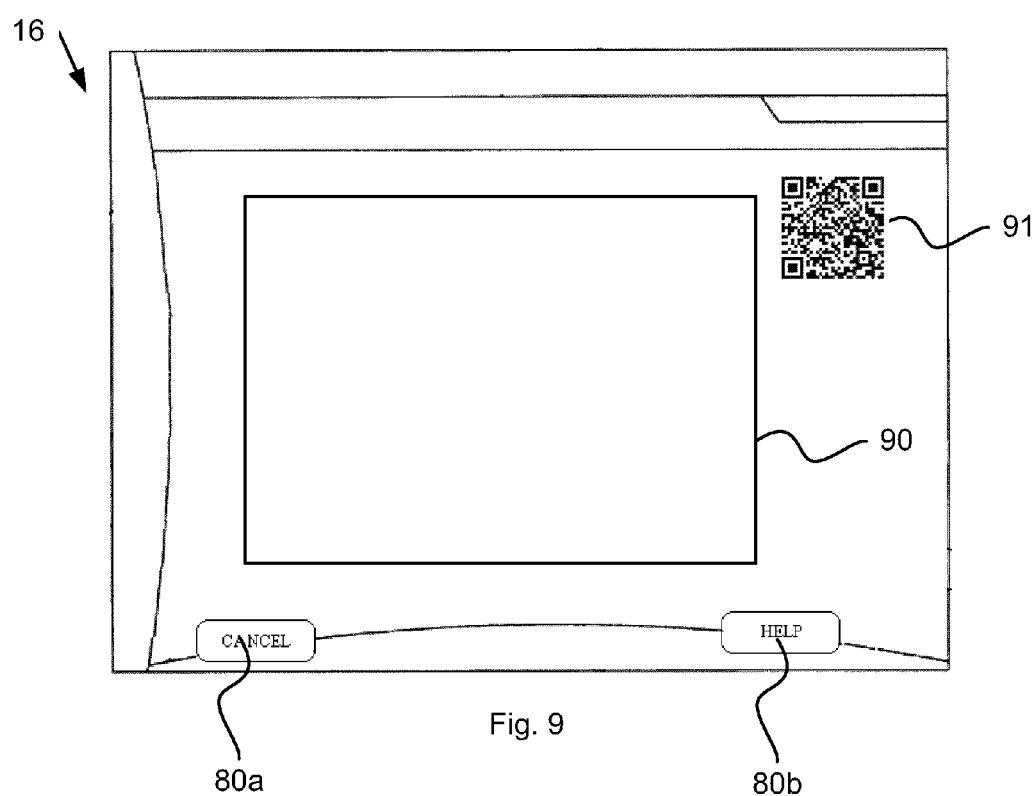

FIG. 9 is an embodiment showing in principle how the display screen of the display 16 could look after executing the abovementioned method. The display 16 may display various graphic elements, as well as functional elements such as actuator buttons 80a, 80b. The display 16 may also display regular information 90 related to the ordinary operation, such as operational parameters, instructions etc. The regular information 90 may also be a human readable version of the data.

Separated from the regular information 90, the machine readable graphical representation 91 may be displayed in a dedicated area of the screen 16. The area of the display 16 displaying the machine readable graphical representation 91 may be touch sensitive, and upon actuation, take the user to the display screen specifically displaying the machine readable graphical representation 81 according to FIG. 8.

In an embodiment, the step of analysing 71 the data involves determining whether a certain apparatus status has occurred, and the step of controlling 72 the displaying involves displaying the machine readable graphical representation in a first display screen on the display 16 when said certain machine status has occurred, and otherwise, alternatively displaying the machine readable graphical representation in a second display screen on the display 16.

An advantage with this is that it enables display differentiation depending on data type, so that some data may be considered critical, and renders a display according to FIG. 8, while other data may render a display according to FIG. 9.

As already stated above, the data pertaining to an operation of the apparatus may be usage specific and selected from the group consisting of usage history, operator interaction history, and treatment parameters.

An advantage with this is that it enables customized support, e.g. since it will be possible to track the use of the apparatus prior to a critical event/malfunction.

The data of the method 60 may also be machine specific for the apparatus 30/dialysis monitor 1 and selected from the group consisting of machine ID, machine configuration data and machine status data. The apparatus may also be configured so that machine specific data comprises contact details of the manufacturer and/or a technical support service, such as phone number or e-mail address. These data may also be held specific to the institution where the apparatus is located. However, the contact details may also be displayed next to the machine readable graphical representation.

An advantage with this is that it allows traceability, since the party receiving the data knows who is sending it. Another advantage is that it simplifies data logging, e.g. since stored data may be classified based on machine specificity.

The data of the method 60 may also be a representation of display screen content at a specific point of time, such as a screen dump.

The step of encoding 62 the data into a machine readable graphic representation may involve encrypting the retrieved data and generating the machine readable graphic representation to represent the encrypted, retrieved data.

An advantage with this is that it increases security. This is particularly an advantage if transmission of the image is to be performed over an insecure communication network, and/or the service of the server is a so called "cloud" application. The security issues for sensitive personal or medical data are readily understood in these cases.

Furthermore, the step of encoding 62 the data into a machine readable graphic representation may involve providing data redundancy in said machine readable graphic representation.

An advantage with this is that it enhances robustness and decreases the risk of error when decoding the machine readable graphical representation. The degree of robustness for different contexts and different types of data has been discussed above. The redundancy can be provided by applying error correcting and/or error detecting codes which enables the server to correct and/or detect, respectively, occurring errors. An error correcting code can provide a "distance", e.g. Hamming distance, between code values, i.e. feasible interpretations, wherein the error correction is performed by selecting a closest or most probable code value from the received image at the server. Error detection can be provided by verification of the received image by using the redundant information.

The step of encoding 62 the data may also comprise a function for data verification, e.g. a checksum function. Thus, in the case of checksum data verification, the remote server may be configured to, after decoding the machine readable graphic representation, send a verification message, such as via SMS, to compare the checksum obtained after decoding with the checksum added to the data by the checksum function before encoding. If the checksums differ, the server may further be configured to request a retransfer of the data.

An advantage with this is that it decreases the risk of misinterpretation due to erroneous data.

In an embodiment, wherein the apparatus has a user interface which comprises said display 16, the method 60 comprises an initial step of providing an actuation element in said user interface for triggering performance of said steps of retrieving 61, encoding 62 and displaying 63.

An advantage with this is that a user may then initiate display of retrieved data.

Said actuation element may be a certain unmarked sub area of a touch-sensitive display screen of said display 16.

An advantage with this is that a user knowing how to initiate display of retrieved data may do so, but an ordinary user is not confused by the option.

The generation of the graphical representation, i.e. the retrieving of data, encoding the data into a machine readable representation and displaying the machine readable representation, can be provided in either of a service context or a treatment context.

The service context means that data relevant to technical service personnel doing service, checking operation, installing updates or additional functions, etc. is retrieved, encoded and displayed, and the service person is able to capture an image of the representation, or in the case of several representations, a sequence of images. The image can then either be stored in the image capturing apparatus for connection to the server at a later time, or be transmitted via a communication network to the server instantly, or as soon as the communication network is accessible. Here, it may for example be prohibited to use wireless transmitters in vicinity of the medical equipment for safety reasons. The site where the medical equipment is located may also be lacking access to communication networks.

Based on the submitted image, the server may respond by transmitting information, e.g. technical information, software updates, or other information that is helpful for the service person to fulfil necessary tasks. The server may alternatively or additionally store information derived from the submitted information as a "service book", i.e. monitoring documentation of performed service tasks, and/or the information may form basis for service plan, charging (e.g. "pay-per-dialysis"), register locking or unlocking of features, etc.

It is a particular advantage that a service person, which may work under very different working conditions throughout the World, can perform the information transmission by depicting the graphical representation and transmitting it to the server, which under certain circumstances needs to be done using an instant camera and sending the image of the representation by fax to a location where the server is located, while under other circumstances, the service person is in possession of more sophisticated apparatus where digital image(s) are decoded and the server, or a mirror of the server, e.g. proxy server, is arranged within the apparatus. The use of so called smartphones can provide for such apparatus, where the server, mirror of the server or proxy server is arranged in the context popularly called an app, i.e. an application which provides for the desired service within the user interface of the smartphone. Thus, the abilities of the visually conveyed data from machine-to-machine end nodes provide for flexibility and versatility, and risk for unintentional changes, as may occur upon conveying data machine-to-man-to-machine, is reduced.

For the treatment context, the technical structure and advantages are similar to those demonstrated for the service context above. However, some particular details are worth mentioning. Where the service context is directed towards the issues of the medical equipment, the treatment context is directed towards issues of operating the medical equipment, and the operation in connection with pre-treatment, e.g. priming, the treatment, e.g. monitoring proper operation, and post-treatment, e.g. cleaning. While it is an advantage that the service person can get information through the visual appearance of the graphical representation without electrically or otherwise affecting the medical equipment and its operation, this is in its context readily understood to be an even more important advantage for the operator during treatment. A further advantage in this context is the reduction of risk of misinterpretations of "machine-to-man" information as of conventional art, and the thereby inherent difficulty of correctly and completely communicating the information observed by a person. The information can be any of information about medical, articles of consumption, technical issues, charging, etc. One example of information can be confirmation of performed operations or operations to be performed where a user that is less skilled, vision impaired, or otherwise feel uncertainty for one or more operation steps can be provided aid in response to conveyed information about current status of the medical equipment. Another example is case book keeping where a nurse can monitor operation of the medical equipment by capturing images of presented graphical representations of performed actions and used parameters. Here, it can be seen that the service context and treatment context may overlap in some sense, at least for some parts, depending on the desired setup.

The versatility of application in different contexts provides for an advantageous solution particularly for small clinics, home treatment and even field treatment where access to different technical means and skills can vary very much.

Depending on the nature of the information to be conveyed by the generation of the graphical representation, its transmission, and then its decoding and use in the server, different levels of robustness and/or amount of information conveyed are chosen. The choice can be based on the context, as demonstrated above, and further be based on the nature of the data for the respective context or sub-context. For example, critical data from a running treatment session may need ample robustness, while some administrative data of routine character may not demand the same robustness. Robustness means here the ability to convey the data by means of quality of the displaying, the image capturing, and the transmission, and can be provided through redundancy of the graphical representation, e.g. in sense of using error correcting and/or error detecting code at the encoding.

Further, depending on the nature of the information, an authorization may be requested from the user, e.g. technical service person, nurse, or patient, to provide the generation of the graphical representation.

Figure 10:
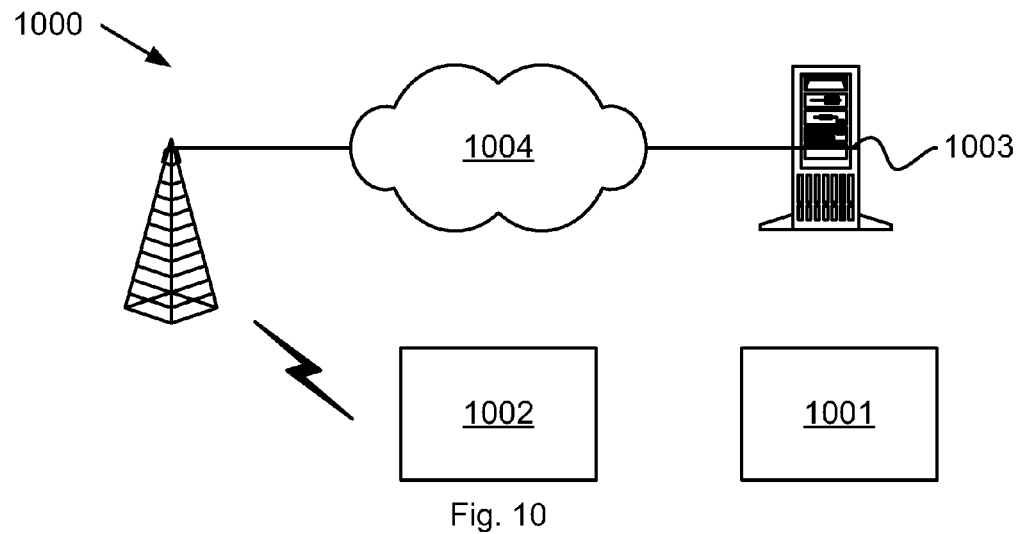
FIG. 10 is an illustration of a system according to an aspect.

In an aspect according to FIG. 10, a system 1000 for transferring data related to the operation of an extracorporeal blood treatment apparatus is provided. The system 1000 comprises an extracorporeal blood treatment apparatus 1001 adapted to perform the method as described above. The system 1000 further comprises an image capturing device 1002 and a remote server 1003 connected to a communication network 1004.

The image capturing device 1002 may be any kind of device adapted to capture the image displayed on the display 16 of the extracorporeal blood treatment apparatus 1001 and transmit captured information, such as the captured image, to said remote server 1003 over a communication channel on the communication network 1004. In an embodiment, the image capturing device 1002 is a cellular phone with a camera. A user (not shown) may then take a photo of the image displayed on the display 16 of the extracorporeal blood treatment apparatus and, when the user is no longer in an environment sensitive to electronic disturbance, send the image over the communication network 1004, which may be a regular cellular phone service network. If the captured information is the image and the image capturing device (1002) is adapted to transmit the captured image to said remote server (1003) encoded, as a machine readable graphical representation, the remote server (1003) is further adapted to receive the transmitted image and decode it to recover the retrieved data.

The image capturing device 1002 is not intended to be connected to the extracorporeal blood treatment apparatus 1001 in any way, except by the optical connection which makes it possible to capture an image. Thus, the total communication channel within the system 1000, i.e. from the extracorporeal blood treatment apparatus 1001 to the remote server 1003, is unidirectional.

In another embodiment, the image capturing device 1002 is a standard digital camera. The image may then be downloaded to a computer and sent over the internet and/or via email.

The image capturing device 1002 may also be a standard mobile phone, with an integrated digital camera. The possibility to use commodity hardware as image capturing devices, instead of specialized reading devices, may be an advantage and facilitates serviceability and enhances user compliance. The image may then be sent from the phone using Multimedia Messaging Service (MMS), or over the Internet and/or via e-mail, or downloaded to a computer and sent over the internet and/or via e-mail.

An advantage with decoding at the remote server 1003 is that the image capturing device 1002 requires no particular decoding ability, such as special software. Thus, any kind of image capturing device 1002 can be used. However, if the image capturing device 1002 has capabilities for decoding a machine readable graphical representation, such as a mobile phone with special software, the captured image may be decoded before transmission of the captured information to the remote server 1003. An advantage with this is that the decoded information may have a smaller size than the encoded image.

The communication network 1004 may be any kind of communication network suitable to provide a communication channel for transfer of the image, such as land base telephone line (including facsimile communication, DSL etc.), optic fiber, LAN, WLAN, internet, email, cellular phone network, surface mail network etc.

The remote server 1003 may be any kind of server suitable to receive the transmitted image and decode it to recover the retrieved data.

The system 1000 may be configured so that the extracorporeal blood treatment apparatus 1001, in operation, is not connected to the communication network 1004.

An advantage with this is that it allows the apparatus to communicate without the need of a continuous connection to a network, which may be detrimental to sensitive neighboring equipment.

The extracorporeal blood treatment apparatus 1001, the image capturing device 1002 and the server 1003 may be physically separated.

In an embodiment, the remote server 1003 is configured to store information from the extracorporeal blood treatment apparatus in a database.

An advantage with this is that it allows data logging, statistical analysis etc.

In a similar way as the medical equipment generates a graphical representation to provide data being in the possession of the medical equipment, the medical equipment can be arranged to capture an image of a machine readable graphical representation to receive data. The data can for example be update information, unlocking or locking keys for features, prescriptions, personal data (e.g. for service person, operator or patient), confirmations from the server mentioned above, etc. The discussions provided above regarding the data, the graphical representation and its encoding, and the multitude of ways to convey the image of the graphical representation applies also in the embodiments where the information flow is towards the medical equipment. For the reading of the graphical representation, the medical equipment needs a camera and/or scanner. The camera works as known in the field of electronic image capturing. The scanner is arranged to sweep the graphical representation with light and detect reflection of the light and thereby register the graphical representation. If the generation of a graphical representation and conveying it to the server demonstrated above is regarded as up-link communication, the here demonstrated conveying of a graphical representation from the server or elsewhere, having the medical equipment of acquire the image by means of the camera or scanner, and decoding the information can be considered as down-link communication.

The image can be received by the operator, e.g. service person, nurse, patient, etc., in many possible ways. As discussed above with regard to terminals connected to a communication network, such as computers, cellphones and smartphones, which accordingly are capable of communicating with the server, or even hold the server, these terminals can produce the graphical representation on their screens, and the terminal can be presented in front of the camera of the medical equipment, and the image of the graphical representation, and thus the down-link data, will reach the medical equipment. In addition to this, the graphical representation can also reach the site of the medical equipment by fax, and even by regular or registered mail. These latter features may seem a bit far-fetched, but in many places in the World, this may be the only feasible way to reach the site by the information, and medical care, and thus necessary down-link information to medical equipment, may be as necessary at such places as elsewhere.

Thus, for such down-link communication there can be provided method for receiving data at an extracorporeal blood treatment apparatus comprising a camera or scanner as an alternative, or additional to the elements elucidated for the visual conveying of machine readable information for the extracorporeal blood treatment apparatus demonstrated above. The method can then comprise acquiring an image of a machine readable graphical representation by the camera or scanner, decoding data of the machine readable graphical representation, and adapting controlling of the operation of the apparatus based on the decoded data. The decoding of the machine readable graphical representation into the data can comprise interpreting a barcode image or a two-dimensional matrix code image of the acquired image. The decoding can further include decrypting data represented by the machine readable graphical representation where encryption is used when generating the graphical representation at a remote, in view of the extracorporeal blood treatment apparatus, location, e.g. at a server. The decoding can further include detecting and/or correcting transmission errors of data represented by the machine readable graphical representation based on redundancy information provided by said machine readable graphical representation.

Figure 12:
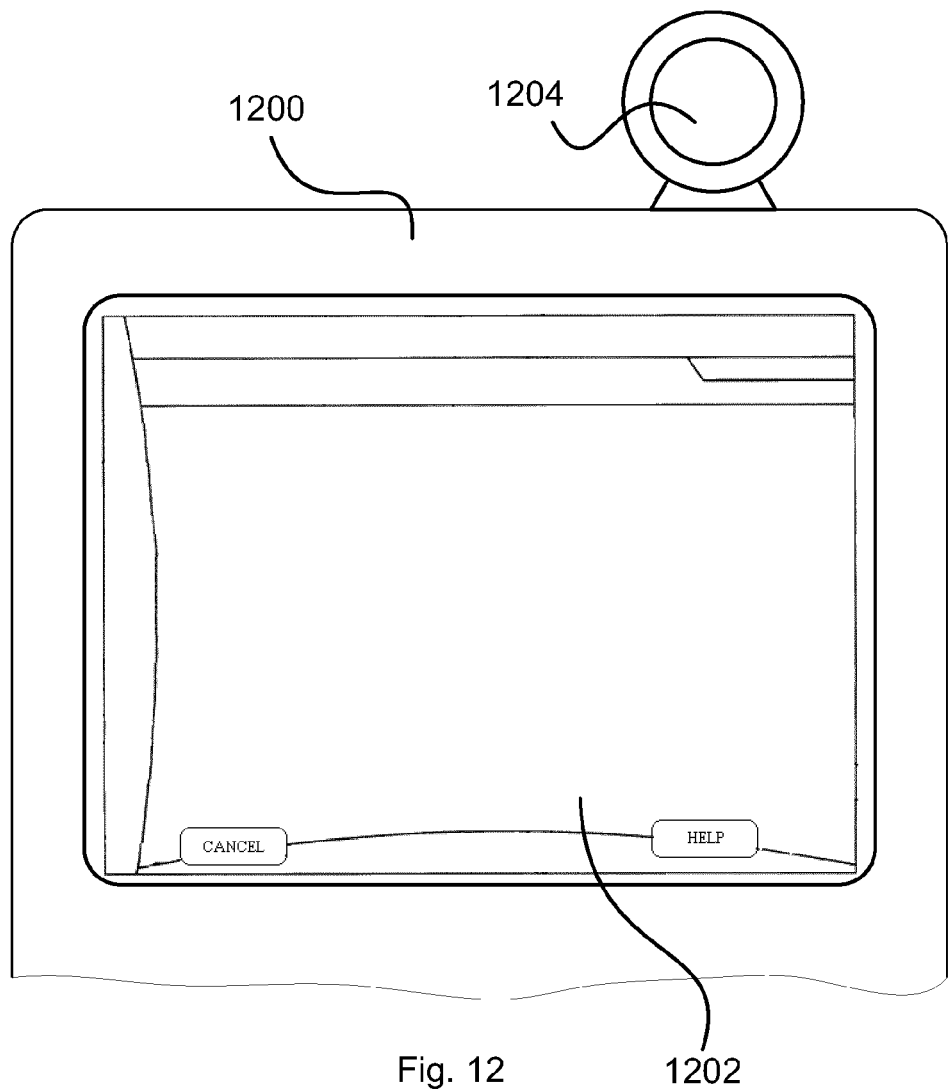
FIG. 12 is a front view of a part of a control module of an extracorporeal blood treatment apparatus, e.g. a dialysis monitor.

Considering two-way communication, i.e. in both up-link and down-link, there can be provided a method for exchanging data for an extracorporeal blood treatment apparatus which then comprises a display and a camera or scanner for the visual conveying of machine readable information to and from the extracorporeal blood treatment apparatus. The method then comprises transferring data according to any of the embodiments demonstrated above for the up-link, and receiving data according to any of the embodiments demonstrated above for the down-link. Preferably, a control module as demonstrated above further comprises the camera or scanner, and is configured to acquire an image of a machine readable graphical representation, decode data of the machine readable graphical representation, and adapt controlling of the operation of the apparatus based on the decoded data. FIG. 12 is a front view of a part of a control module of an extracorporeal blood treatment apparatus 1200, e.g. a dialysis monitor, which includes a display 1202 and a camera or scanner 1204.

As will be appreciate by the person skilled in the art, an apparatus according to an aspect of the invention may be part of a larger system of different apparatuses. Thus, in an embodiment the apparatus is comprised in a medical workstation or medical system, such as a Computed Tomography (CT) system, Magnetic Resonance Imaging (MRI) System or Ultrasound Imaging (US) system.

Figure 11:
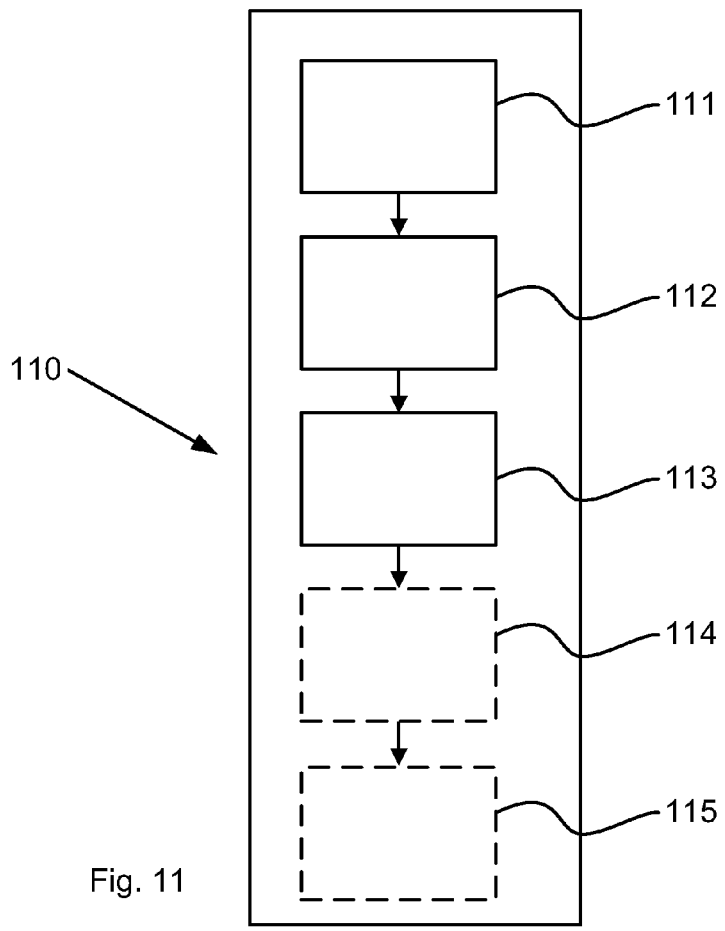
FIG. 11 is a schematic overview of a computer-readable medium according to an aspect.

In an aspect according to FIG. 11, a computer-readable medium 110 for processing by a computer is provided. The computer-readable medium 110 has embodied thereon a computer program for transferring data from an extracorporeal blood treatment apparatus comprising a display and at least one control unit. The computer program comprises a first code segment 111 for retrieving data pertaining to an operation of the apparatus and a second code segment 112 for encoding the data into a machine readable graphical representation adapted for decoding at a remote server to recover the retrieved data. The computer program further comprises a third code segment 113 for displaying the machine readable graphical representation as an image on the display to allow capture of the displayed image with an image capturing device and transmission of the image from the image capturing device to said remote server over a communication channel.

The computer-readable medium may optionally also comprise a fourth code segment 114 for analysing the data before encoding and a fifth code segment 115 for controlling the displaying of the machine readable graphical representation depending on an outcome of the data analysis.

The invention may be implemented in any suitable form including hardware, software, firmware or any combination of these. However, preferably, the invention is implemented as computer software running on one or more data processors and/or digital signal processors. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly be combined, and the inclusion in different claims does not imply that a combination of features is not feasible. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. An extracorporeal blood treatment apparatus comprising a display and a control module, wherein the control module is configured to:
retrieve data pertaining to an operation of the extracorporeal blood treatment apparatus;
analyse the data to determine whether a certain apparatus status has occurred;
encode the data into a machine readable graphical representation adapted for presentation on the display, wherein the machine readable graphical representation is adapted to be decoded at a remote server to recover the retrieved data; and
display the machine readable graphical representation on the display, wherein the machine readable graphical representation is displayed on a first screen of the display when the certain apparatus status has occurred, and the machine readable graphical representation is displayed on a second screen of the display if the certain apparatus status has not occurred.

2. The extracorporeal blood treatment apparatus of claim 1, wherein the control module comprises a processor and non-transitory memory storing an operating system and program instructions which are executed by the processor to cause the control module to perform the steps of retrieving the data, analysing the data, encoding the data and displaying the machine readable graphical representation.

3. The extracorporeal blood treatment apparatus according to claim 1, further comprising a user interface including said display, wherein the user interface has an actuation element for triggering performance of the control module.

4. The extracorporeal blood treatment apparatus according to claim 1, wherein the control module for the extracorporeal treatment apparatus is configured to encode the data into at least two machine readable graphical representations adapted for sequential display on the display and further adapted to be decoded at the remote server to recover the retrieved data.

5. The extracorporeal blood treatment apparatus according to claim 1, wherein the control module is configured to encode the data into at least two machine readable graphical representations adapted for sequential display on the display as a film and further adapted for decoding at a remote server to recover the retrieved data.

6. The extracorporeal blood treatment apparatus according to claim 1, wherein the display is in a dialysis monitor.

7. The extracorporeal blood treatment apparatus according to claim 1, further comprising a camera or scanner, and the apparatus configured to:
acquire an image of an additional machine readable graphical representation with the camera or scanner;
decode data of the machine readable graphical representation, and
adapt controlling of an operation of the apparatus based on the decoded data.

8. The extracorporeal blood treatment apparatus of claim 1, wherein the data comprises usage specific data pertaining to usage of the apparatus during its operation for extracorporeal blood treatment.

9. A system for transferring data related to the operation of an extracorporeal blood treatment apparatus, the system comprising:
an extracorporeal blood treatment apparatus including a display and a control module, wherein the control module is configured to (i) retrieve data pertaining to an operation of the extracorporeal blood treatment apparatus, (ii) analyse the data to determine whether a certain apparatus status has occurred, (iii) encode the data into a machine readable graphical representation adapted for presentation on the display, and (iv) display the machine readable graphical representation as an image on the display, wherein the machine readable graphical representation is displayed on a first screen of the display when said certain apparatus status has occurred, and the machine readable graphical representation is displayed on a second screen of the display if the certain apparatus status has not occurred;
an image capturing device; and
a remote server connected to a communication network, wherein the image capturing device is adapted to capture the image displayed on the display of the extracorporeal blood treatment apparatus and transmit information regarding the captured image to said remote server through the communication network, and
wherein the remote server is adapted to receive the transmitted information and recover from the transmitted information the retrieved data.

10. The system according to claim 9, wherein the transmitted data includes the image captured by the image capturing device, and the remote server is further adapted to receive the transmitted image and decode it to recover the retrieved data.

11. The system according to claim 9, wherein the extracorporeal blood treatment apparatus, when in operation, is not connected to said communication network.

12. The system according to claim 9, wherein the extracorporeal blood treatment apparatus, the image capturing device and the remote server are physically separated.

13. The system according to claim 9, wherein the remote server includes a non-transitory storage device storing within a database the data received from the extracorporeal blood treatment apparatus.

14. The system according to claim 9, further comprising:
an image presentation device adapted to receive image information from said remote server over a communication channel on the communication network, and display a received machine readable graphical representation to enable a camera of the extracorporeal blood treatment apparatus to register the image of the machine readable graphical representation such that the control module is enabled to decode data of the machine readable graphical representation and adapt controlling of the operation of the extracorporeal blood treatment apparatus based on the decoded data.

15. The system according to claim 9, wherein the data comprises usage specific data pertaining to usage of the apparatus during its operation for extracorporeal blood treatment.

16. A non-transitory computer-readable medium having embodied thereon a computer program for transferring data from an extracorporeal blood treatment apparatus comprising a display and at least one control unit, for processing by a computer, the computer program comprising:
- a first code segment for retrieving data pertaining to an operation of the extracorporeal blood treatment apparatus;
- a second code segment for analysing the data to determine whether a certain apparatus status has occurred;
- a third code segment for encoding the data into a machine readable graphical representation adapted for decoding at a remote server to recover the retrieved data; and
- a fourth code segment for displaying the machine readable graphical representation as an image on the display to allow capture of the displayed image with an image capturing device and transmission of the image from the image capturing device to said remote server over a communication channel,
- wherein the machine readable graphical representation is displayed on a first screen of the display when said certain apparatus status has occurred, and the machine readable graphical representation is displayed on a second screen of the display if the certain apparatus status has not occurred.

17. The non-transitory computer-readable medium according to claim 16, further comprising:
- a fifth code segment for controlling the displaying of the machine readable graphical representation depending on an outcome of the data analysis.

18. The non-transitory computer-readable medium according to claim 16, wherein the data comprises usage specific data pertaining to usage of the apparatus during its operation for extracorporeal blood treatment.

19. A method for transferring data from an extracorporeal blood treatment apparatus including a display and at least one control unit, the method comprising:
- retrieving data pertaining to an operation of the apparatus;
- analysing the data to determine whether a certain apparatus status has occurred;
- encoding the data into a machine readable graphical representation adapted for decoding at a remote server to recover the retrieved data;
- displaying the machine readable graphical representation as an image on the display to allow capture of the displayed image with an image capturing device, wherein the machine readable graphical representation is displayed in a first display screen on the display when said certain apparatus status has occurred, and the machine readable graphical representation is displayed in a second display screen on the display if the certain apparatus status has not occurred; and
- transmitting the image from the image capturing device to said remote server over a communication channel.

20. The method according to claim 19, wherein the data comprises machine specific data for said apparatus, the machine specific data being selected from a group consisting of machine ID, machine configuration data and machine status data.

21. The method according to claim 19, wherein the data comprises usage specific data selected from a group consisting of usage history, operator interaction history, and treatment parameters used by the apparatus during its operation for extracorporeal blood treatment.

22. The method according to claim 19, wherein encoding the data into a machine readable graphic representation involves generating a barcode image or a two-dimensional matrix code image to represent the retrieved data.

23. The method according to claim 19, wherein encoding the data into a machine readable graphic representation involves encrypting the retrieved data and generating the machine readable graphic representation to represent the encrypted, retrieved data.

24. The method according to claim 19, said apparatus having a user interface which comprises said display, the method comprising an initial step of providing an actuation element in said user interface for triggering performance of said steps of retrieving, analysing, encoding and displaying.

25. The method according to claim 24, wherein said actuation element is a certain unmarked area of a touch-sensitive display screen of said display.

26. The method according to claim 19, the blood treatment apparatus further including a camera or scanner and at least one control unit, the method further comprising:
- acquiring with the camera or scanner an image of an additional machine readable graphical representation and generating data representative of the additional machine readable graphical representation;
- decoding the data of the additional machine readable graphical representation; and
- controlling of the operation of the blood treatment apparatus based on the decoded data.

27. The method according to claim 26, wherein the decoding of the additional machine readable graphical representation into said data comprises interpreting a barcode image or a two-dimensional matrix code image of the acquired image.

28. The method according to claim 26, wherein the decoding further includes decrypting data represented by the additional machine readable graphical representation.

29. The method according to claim 19, wherein the data comprises usage specific data pertaining to usage of the apparatus during its operation for extracorporeal blood treatment.

* * * * *